(12) United States Patent
Garcia-Rubio et al.

(10) Patent No.: US 7,027,134 B1
(45) Date of Patent: Apr. 11, 2006

(54) SPECTROPHOTOMETRIC SYSTEM AND METHOD FOR THE IDENTIFICATION AND CHARACTERIZATION OF A PARTICLE IN A BODILY FLUID

(75) Inventors: Luis H. Garcia-Rubio, Temple Terrace, FL (US); Catalina E. Alupoaei, Hillsboro, OR (US); Willard Harris, Lutz, FL (US); Alfredo Peguero, Tampa, FL (US); Edward P. Cutolo, Tampa, FL (US); German Felix Leparc, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/934,601

(22) Filed: Sep. 3, 2004

Related U.S. Application Data

(60) Continuation of application No. 10/249,637, filed on Apr. 28, 2003, now Pat. No. 6,788,394, and a continuation-in-part of application No. 09/861,781, filed on May 21, 2001, which is a division of application No. 09/206,630, filed on Dec. 7, 1998, now abandoned, which is a continuation-in-part of application No. 08/775,645, filed on Dec. 31, 1996, now Pat. No. 5,839,850, which is a continuation-in-part of application No. 08/385,717, filed on Feb. 8, 1995, now Pat. No. 5,589,932, said application No. 10/249,637 is a continuation of application No. 09/904,107, filed on Jul. 12, 2001, now abandoned.

(60) Provisional application No. 60/217,742, filed on Jul. 12, 2000.

(51) Int. Cl.
*G01N 33/48* (2006.01)

(52) U.S. Cl. .................. 356/39; 600/310; 600/314
(58) Field of Classification Search ............ 356/39–41, 356/335, 337, 441, 433, 300–334; 600/310, 600/314
See application file for complete search history.

(56) References Cited

U.S. PATENT DOCUMENTS 4,935,147 A * 6/1990 Ullman et al. .............. 210/695
6,788,394 B1 * 9/2004 Garcia-Rubio et al. ....... 356/39

* cited by examiner

*Primary Examiner*—Michael P. Stafira
*Assistant Examiner*—Juan D. Valentin, II
(74) *Attorney, Agent, or Firm*—Smith & Hopen, P.A.; Molly L. Sauter

(57) ABSTRACT

The present invention provides a method and apparatus for the detection of an infectious disease or disorder in a fluid, such as a mammalian blood sample, the detection of a specific protein in a urine sample, or the detection of a particle in a plasma. The identification of the particles of interest is enable by taking a transmission spectrum of a test sample in at least a portion of the ultraviolet, visible, near-infrared portion of the spectrum and comparing the spectrum with a standard sample spectrum. From the comparison it is then determined whether the fluid from the test sample contains an particle of interest, and an identity of the particle of interest is determined. Spectroscopic and multi-wavelength turbidimetry techniques provide a rapid, inexpensive, and convenient means for diagnosis. The comparison and determination steps may be performed visually or by spectral deconvolution.

50 Claims, 17 Drawing Sheets

Fig. 7

| Table 1. Malaria Patient Information |||||||
|---|---|---|---|---|---|
| Malaria Patient | Species | Symptoms Noted | Diagnosed | Treated | Spectroscopy |
| 1 | F | day 1 | day 10 | 7 days | day 17 |
| 2 | F | day 1 | no data | no data | day 17 |
| 3 | V | day 1 | day 4 | 4 days | day 17 |
| 4 | Suspected | no data | no data | no data | day 17 |

Fig. 8

| Table 2. Dengue Fever Patient Information ||||||
|---|---|---|---|---|---|
| Dengue Fever | Type | Symptoms | Clinic Diagnosis | Laboratory Diagnosis | Spectroscopy |
| 1 | H | day 1 | day 5 | no data | day 21 |
| 2 | C | day 1 | day 2 | day 4 | day 7 |
| 3 | C | day 1 | day 3 | day 6 | day 19 |
| 4 | C | day 1 | day 3 | no data | day 30 |

Three Most Common Microbial Contaminants

SPECTROPHOTOMETRIC SYSTEM AND METHOD FOR THE IDENTIFICATION AND CHARACTERIZATION OF A PARTICLE IN A BODILY FLUID

CROSS-REFERENCE TO RELATED APPLICATION

This application is a continuation of U.S. patent application Ser. No. 10/249,637, filed Apr. 28, 2003 now U.S. Pat. No. 6,788,394, which is a continuation of abandoned U.S. application Ser. No. 09/904,107, filed Jul. 12, 2001, which claims priority from commonly owned provisional application Ser. No. 60/217,742, filed Jul. 12, 2000, the disclosure of which is incorporated herein by reference. This application is also a continuation-in-part of co-pending U.S. application Ser. No. 09/861,781, filed May 21, 2001, which is a divisional of U.S. application Ser. No. 09/206,630 filed Dec. 7, 1998 now abandoned, which is a continuation-in-part of U.S. application Ser. No. 08/775,645 filed Dec. 31, 1996, now U.S. Pat. No. 5,839,850 issued on Nov. 24, 1998, which is a continuation-in-part of U.S. application Ser. No. 08/385,717 filed Feb. 8, 1995, now U.S. Pat. No. 5,589,932 issued on Dec. 31, 1996.

FIELD OF THE INVENTION

The present invention relates to a spectroscopic system and methods for the identification and characterization of particles in a fluid, and, more particularly, to such systems and methods for the identification and characterization of particles in a bodily fluid.

BACKGROUND OF INVENTION

A critical limitation in the area of disease identification, diagnosis, and prevention has been the lack of simple, rapid, and effective screening techniques. This problem is particularly acute in locations and/or situations where rapid analysis and diagnosis may involve decisions concerning life-threatening circumstances such as natural disasters or combat, and where the need for portable laboratories is accentuated by the remoteness of areas where diseases are endemic and where epidemics are generated. In addition, in the medical field there is a considerable need for the identification of markers that permit the diagnosis and treatment of diseases early in their development stage and thus avoid lengthy periods of incubation, which invariably worsen the condition of the patient.

Typically, microorganisms and viruses of concern have sizes ranging between 0.5 and 20 pm and, in many cases, are present in fairly dilute concentrations. Although the analytical instrumentation used in medical and clinical laboratories has improved considerably over the past decade to the present, there are still no suitable techniques capable of detecting, classifying, and counting microorganisms in bodily fluids.

Technology known in the art requires that the presence of target microorganisms be detected using microscopy and/or immunoassay techniques. These require a significant amount of time, trained technicians, and well-equipped laboratory facilities.

The costs associated with current laboratory techniques for disease identification and diagnosis therefore further accentuate the need for the development of rapid screening methods.

Another limitation of the currently employed technology is a lack of on-line capability and continuous measurement capabilities for the characterization of blood and other fluid components, as well as a lack of portable instrumentation capable of detecting, counting, and classifying specific blood and other fluid components. The problem of portable instrumentation and suitable methods of analysis and diagnosis is particularly relevant to the medical industry, where the need for rapid analysis and diagnosis often involves life-threatening situations. Although the analytical instrumentation used in medical and clinical laboratories has improved considerably over the past decade, there are still no suitable techniques capable of detecting, classifying, and counting on-line critical cell populations and/or pathogens in blood and other bodily fluids.

Blood cell component counting technology known in the art uses, for example, red cell counts, platelet counts, and white cell counts as indicators of the state of disease. White blood cells can be difficult to count if they are present in small numbers. At present automated hematology analyzers that employ light scattering or impedance techniques are used, but these can introduce a high error rate when determining counts for low sample numbers. In cases of leukoreduced blood products with lower numbers of white blood cells, staining and microscopy or flow cytometry are typically used.

As is known from spectroscopy theory, a measure of the absorption of the attenuation of light through a solution or a suspension is the extinction coefficient, which also provides a measure of the turbidity and transmission properties of a sample. Spectra in the visible region of the electromagnetic spectrum reflect the presence of metal ions and large conjugated aromatic structures and double-bond systems. In the near-ultraviolet (uv) region small conjugated ring systems affect absorption properties. However, suspensions of very large particles are powerful scatterers of radiation, and in the case of cells and microorganisms, the light scattering effect can be sufficiently strong to overwhelm absorption effects. It is therefore known to use uv-vis spectroscopy to monitor purity, concentration, and reaction rates of such large particles and their suspending media.

The detection of trace amounts of albumin in urine has been developed into an important tool for the diagnosis and monitoring of renal and heart diseases. The main difficulty in the detection of albumin and other proteins arises from the relatively weak absorption coefficients of the protein chromophoric amino acids. This requires either high concentrations for detection, or the incorporation of stronger chromophores or fluorophores to enable spectrophotometric detection. Alternatively, the use of antibodies attached to micro-spheres is also a means of collecting the protein and enabling detection. Although existing methods have the required sensitivity (reproducible detection down to 10 mg/L) they are expensive and in many instances semi quantitative only.

Many attempts have been made to estimate the particle size distribution (PSD) and the chemical composition of suspended particles using optical spectral extinction (transmission) measurements. However, previously used techniques neglect the effects of the chemical composition and require that either the form of the P80 be known a priori or that the shape of the PSD be assumed. One of the present inventors has applied standard regularization techniques to the solution of the transmission equation and has demonstrated correct PSDs of a large variety of polymer lathces, protein aggregates, silicon dioxide and alumina particles, and microorganisms.

It has also been known to use the complementary information available from simultaneous absorption and light scattering measurements at multiple angles for the characterization of the composition and molecular weight and shape of macromolecules and suspended particles (Garcia-Rubio, 1993; and U.S. Pat. No. 5,808,738), the disclosure of which is incorporated herein by reference.

Interferometric techniques are known in the art for cell classification (Cabib et at., U.S. Pat. Nos. 5,991,028 and 5,784,162) which use fluorescence microscopy with stained cells. Fluorescence and reflection spectroscopy can also be used to characterize a material by sensing a single wavelength (Lemelson, U.S. Pat. Nos. 5,995,866; 5,735,276; and 5,948,272), which can detect organisms in a bodily fluid. Electroluminescence may also be used to detect an analyte in a sample (Massey et at., U.S. Pat. No. 5,935,779). Cell counting may be accomplished by vibrational spectroscopy (Zakim et al. U.S. Pat. No. 5,733,739). Infrared techniques can detect cellular abnormalities (Cohenford et al., U.S. Pat. Nos. 6,146,897 and 5,976,885; Sodickson et al., U.S. Pat. No. 6,028,311).

One of the present inventors previously developed ultraviolet-visible spectroscopic techniques for detecting and classifying microorganisms in water (Garcia Rubio, U.S. Pat. No. 5,616,457), for characterizing blood and blood types (Garcia Rublo, U.S. Pat. No. 5,589,932), and, as mentioned above, for characterizing particles with a multiangle-multiwavelength system (Garcia-Rubio et at., U.S. Pat. No. 5,808,738). The disclosures of these patents are incorporated herein by reference.

The optical spectral extinction of particle dispersions (combined absorption and scattering characteristics) contains information that, in principle, can be used to estimate the size distribution (PSD) and the chemical composition of the suspended particles. This extinction as a function of wavelength can be obtained from a variety of optical configurations including transmission measurements (Bohren and Huffman, 1983), angular scattering measurements (van de Hulst, 1969) and through the use of integrating spheres (Kortum, 1969). A large number of techniques for the estimation of the PSD from turbidity measurements have been reported (van de Hulst, 1957; Kerker, 1969; Wallach et al., 1961; Zollars, 1980; Melik and Fogler, 1983). Most of these techniques require that either the form of the particle size distribution be known a priori, or that the shape of the PSD be assumed (Zollars, 1980, Melik and Fogler, 1983). Regularization techniques, which make no assumptions regarding the shape of the particle size distribution (Towmey, 1979; Golub et al., 1979; Tarantola, 1987), have been applied to the interpretation of transmission spectra (Elicabe and Garcia-Rubio, 1990, 1988). The regularized solution has been shown to yield the correct particle size distribution and the chemical composition for a large variety of polymer lattices (Brandolin and Garcia-Rubio, 1991), protein aggregates (Garcia-Rubio et al. 1993), SiO$_2$ particles (Koumarioti et al, 1999) and whole blood and blood components (Mattley et al. 2000, Garcia-Rubio, unpublished data). The equation that relates the turbidity ($\tau(\lambda_0)$) measured at a given wavelength $\lambda_0$ and the normalized particle size distribution for spherical particles (f(D)) is given by (Van de Hulst, 1957, Kerker, 1969):

$$\tau(\lambda_0) = Np\left(\frac{\pi}{4}\right)\int_0^\infty Q_{ext}(m(\lambda_0), D)D^2 f(d)\,dD \quad (1)$$

Where D is the effective particle diameter, $Q_{ext}(m(\lambda_0),D)$ corresponds to Mie extinction coefficient, and Np is the number of particles per unit volume. The Mie extinction coefficient is a function of the optical properties of the particles and suspending medium through the complex refractive index ($m(\lambda_0)$) given in Equation 2.

$$m(\lambda_0) = \frac{n(\lambda_0) + i\kappa(\lambda_0)}{n_0(\lambda_0)} \quad (2)$$

where $n(\lambda_0)$ and $n_0(\lambda_0)$ correspond to the refractive index of the particles and the suspending medium, respectively. The absorption coefficient of the suspended particles is represented by $\kappa(\lambda_0)$.

Equation 1 can be written in matrix form by discretizing the integral with an appropriate quadrature approximation (Elicabe and Garcia-Rubio, 1990; Elicabe and Garcia-Rubio, 1988):

$$\underline{\tau} = A\underline{f} + \underline{\varepsilon} \quad (3)$$

Where a composite of experimental errors is represented, errors due to the model approximations and the errors introduced by the discretization procedure (Elicabe and Garcia-Rubio, 1990). Equation 4 gives the regularized solution to Equation 3:

$$\hat{\underline{f}}(\gamma) = (A^T A + \gamma H)^{-1} A^T \underline{\tau} \quad (4)$$

Where H is a covariance matrix that essentially filters the experimental and the approximation errors; the regularization parameter is estimated using the Generalized Cross-Validation technique (GCV) (Golub et al., 1979). The Generalized Cross-Validation technique requires the minimization of Equation 5 with respect to the regularization parameter (Golub et al., 1979; Elicabe and Garcia-Rubio, 1990):

$$V(\gamma) = N ob \frac{\left|(I - A(A^T A + \gamma H)^{-1} \underline{\tau}\right|^2}{\text{Trace}\left[(I - A(A^T A + \gamma H)^{-1} A^T\right]^2} \quad (5)$$

Nob represents the number of discrete turbidity measurements. Simultaneous application of Equations 4 and 5 to the measured turbidity spectra yields the spherical-equivalent discretized particle size distribution.

Equations 1–5 can be used in a variety of ways depending on the information sought and the data available. For example, if the optical properties are known as functions of wavelength (i.e., the contribution from the chromophoric groups in the spectral region of interest), Equations 4–5 can be used to estimate the particle size distribution. Alternatively, if the particle size distribution is known (i.e. from microscopy, centrifugation, chromatography, sedimentation or other techniques), Equations 1, 2 and 4 can be used to estimate the optical properties, and therefore the chemical composition, of the particles and of the fluid of interest. Clearly, if the particles present have a variety of shapes, the optical properties obtained may not be completely accurate.

Nevertheless, these effective optical property values are tantamount to a calibration and can be used to classify (fingerprint) and identify distinct particle and aggregate populations. This approach has been effectively applied to the analysis of platelets (see Mattley et. al, 2000) and for the characterization of bacterium vegetative cells and spores (see Alupoaei et al. 2002).

SUMMARY OF THE INVENTION

It is therefore an object of the present invention to provide a system and method for identifying and diagnosing an infectious disease.

It is a further object to provide such a system and method for identifying and diagnosing such an infectious disease in the bloodstream.

It is another object to provide such a system and method for identifying and diagnosing such an infectious disease in another bodily fluid.

It is an additional object to provide such a system and method for identifying and diagnosing a blood disease.

It is yet a further object to provide such a system and method for identifying and diagnosing a disease that affects the size, shape, and/or chemical composition of a particulate or other component in a bodily fluid.

It is yet another object to provide such a system and method that are operable in a remote location.

These and other objects are achieved by the present invention, a method for detecting a presence of and identifying an infectious disease or disorder in a mammalian blood sample. Herein the word disorder is intended in its broadest sense, that is, as any abnormality detectable over a known range of characteristics of the measured particulates or suspending medium.

The method comprises the steps of taking a multiwavelength spectroscopy measurement, typically a transmission spectrum of a test blood sample in at least a portion of the ultraviolet visible near-infrared range of the electromagnetic spectrum and comparing the spectrum with a standard blood sample spectrum known to be free from the infectious disease or disorder. From the comparison it is then determined whether the blood from the test sample contains the infectious disease or disorder, and an identity of the infectious disease or disorder is determined.

Spectroscopic and multiwavelength turbidimetry techniques provide a rapid, inexpensive, and convenient means for diagnosis. As a first embodiment, the comparison and determination steps may be performed visually, since the signatures of certain diseases and disorders are so strong; in another embodiment it has been found that the spectral deconvolution of the turbidimetric spectra can provide additional and more detailed qualitative and quantitative information. Both embodiments of the invention can rapidly and inexpensively achieve disease diagnosis in remote locations and at a natural disaster, epidemic, or combat site.

In a particular subembodiment, a change in a blood particle or other component caused by an infectious agent or disorder is detected spectroscopically. Such a change may comprise, for example, a shape change, such as occurs with sickle cell anemia, or a lysis, for example, of a red blood cell, which releases free hemoglobin and bilirubin into the blood plasma.

In another subembodiment the test sample may comprise another bodily fluid for detecting a presence of an infectious disease or disorder.

In a specific embodiment, the test sample may comprise urine for detecting the presence and amount of albumin for the diagnosis and monitoring of renal and heart diseases. In a specific embodiment, the detection of trace amounts of albumin in urine (Albuminuria) has been developed into an important tool for diagnosis and monitoring of renal and heart diseases. A suitable device that could be used at home to measure the levels of albumin and creatinine in urine would help to prevent, detect, diagnose, treat, follow, and manage diseases that disable and kill millions of people each year. To be successful, the device should be small, portable, attractive, safe, easy and simple to use, accurate, scientifically valid, reliable, sturdy and long-lived, and capable of instantly timing, displaying, recording, and storing its results (the urine concentrations of albumin and creatinine and the ratio of albumin concentration to creatinine concentration) while simultaneously and effortlessly sending these results digitally and electronically, regardless of distance, from the home to a clinic, health care provider, or data center. Through a simple modification of the standard spectrophotometric methods for the detection of proteins as described by the present invention, it is possible to quantify the amount of albumin in urine at a minimal cost, and to incorporate it within the protocol for standard urine analysis. The measurements can be conducted at the office, in a laboratory setting, or at home thus enabling repeated samples to be taken through the day. A technique based on protein aggregation followed with multiwavelength spectrophotometric measurements constitutes the basis of this embodiment of the present invention. The use of salts for protein aggregation and precipitation is very well established in the art. When proteins aggregate, there are significant changes in the absorption and scattering properties of the suspension. These changes are quantitative and considerably amplify the spectrophotometric response, thus enabling quantitative detection down to 10 mg/L. The novelty of this embodiment is the use of proven protein precipitation methods with sensitive quantitative multiwavelength spectrophotometric techniques for the detection of microabluminuria.

In an additional embodiment, the method of the present invention is utilized for the detection of platelets and microorganisms in plasma.

The inventive method is based on multiwavelength spectroscopy measurements and the interpretation of the absorption and scattering properties of single particles from a plurality of populations and their suspending media. The spectroscopy measurements may comprise transmission, reflectance, and multiangle, multiwavelength, using either polarized or unpolarized light, in the uv-vis near-infrared portions of the electromagnetic spectrum. Unlike microscopy measurements, the samples typically comprise cells in the range of 106 particles. The analytical method yields such information as, but not intended to be limited to, particle counts, compositional analysis, size, and shape of the particulates and the suspending media.

The invention is believed to provide a multiplicity of improvements over the prior art in achieving a rapid, inexpensive, and convenient means for characterization and detection of particulates in a bodily fluid, including characterization of such particulates as, but not intended to be limited to, cell shapes, blood antigens, microorganisms, and viruses. The rapidity and portability of the system of the invention permits its use in critical conditions such as epidemics and combat and also in remote and/or technology-disadvantaged locations.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 7 is table 1 which provides accompanying malaria diagnosis data provided by the Laboratorio Regional de Apoyo Epidemiologica, Valencia, Venezuela.

FIG. 8 is table 2, which provides accompanying dengue fever diagnosis data provided by the Laboratorio Regional de Apoyo Epidemiologica, Valencia, Venezuela.

DETAILED DESCRIPTION OF THE PREFERRED EMBODIMENTS

A description of the preferred embodiments of the present invention will now be presented with reference to FIGS. 1–8.

The system of the present invention comprises any of known standard spectrometers, such as a portable fiber optics-based spectrophotometer for laboratory testing, in situ measurements, and field applications. The spectrophotometer should be capable of recording the transmission, reflectance, or angular backscattering spectra of blood and other bodily fluids, neat, in solution, and in situ, in any combination or portion of the ultraviolet, visible, and near-infrared portions of the electromagnetic spectrum, preferably with a resolution of at least 2 nm. Recent developments in miniature spectrometer technology permit the use of portable multiprobe integrated systems for rapid blood characterization and diagnosis within the scope of the present invention.

Figure 1:
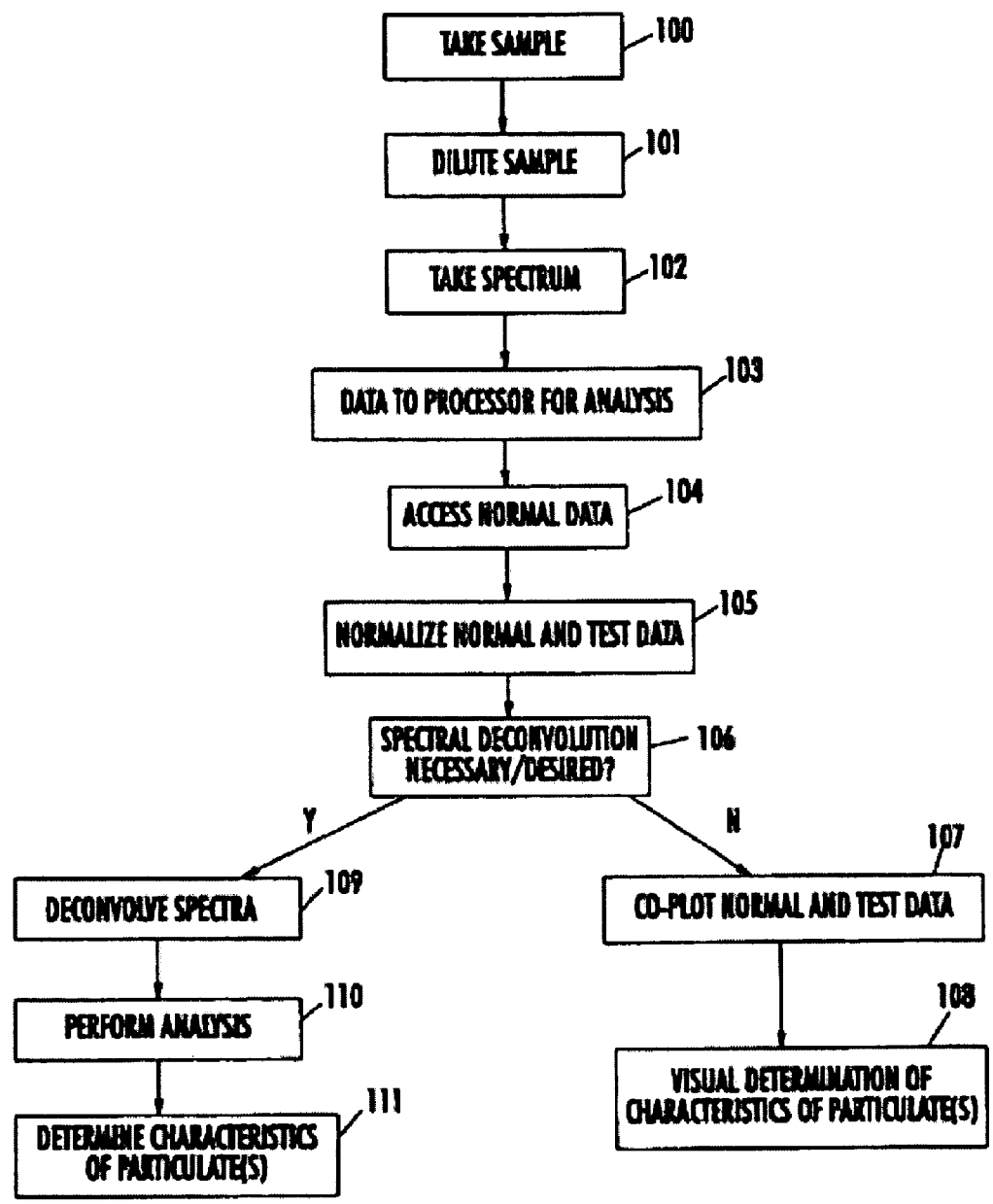
FIG. 1 is a flow chart of the method of the present invention.

An exemplary method of analyzing a fluid sample for the presence of particulates, their characteristics, and that of the suspending medium is shown in the flow chart of FIG. 1. A sample, such as a blood sample, is taken (block 100) and diluted (when appropriate) (block 101) to a concentration level for spectrophotometer linearity, typically 4000 cells per microliter for whole blood. This number is not intended as a limitation, and it will be understood by one of skill in the art that such values are likely to change with the introduction and alteration of technology in the field. An exemplary figure for use at present comprises 1.5 Au.

An exemplary blood dilution protocol is followed for the detection of, for example, a tropical disease, which comprises drawing a whole blood sample into an anticoagulant and diluting substantially 1:1000 with physiological saline. One dilution tube for each whole blood sample that is to be analyzed is prepared by pipetting 3 mL of saline into the tube and adding 3 pL blood, after wiping the outside of the pipette tip to remove excess whole blood. The sample is mixed by inverting the cuvette gently three times.

If dilution tubes are not available, the whole blood can be diluted directly into a cuvette by adding 2 pL whole blood into 2 mL saline in the cuvette. Alternatively, the sample can be placed in a thin measurement cell such that the complete transmission spectrum can be recorded in accordance with known spectroscopy practices.

If the diluted sample is above 1.5 absorbance units in the spectral region measured from 240 to 800 nm, an additional 0.5 mL saline should be added directly to the cuvette and mixed by inverting gently three times. If the spectrum is still too strong, repeat the saline addition until the spectrum is below 1.5 absorbance units. Alternatively, if the spectrum is too concentrated (above 1.5 absorbance units), a new whole blood dilution can be prepared by using less whole blood (e.g., 2 pL whole blood into 3 mL saline).

If the diluted blood sample is below 0.2 absorbance units in the spectral region measured from 240 to 800 nm, prepare a new whole blood dilution using more whole blood (e.g., 4 ii whole blood in 3 mL saline). Similar effects can be accomplished by adjusting the path length of the measurement cell in accordance with standard spectroscopy practices.

In a particular embodiment, the cuvette should be rinsed five times with deionized water before measuring the spectrum of another diluted blood sample.

After all the samples have been analyzed each day, the cuvette should be cleaned by filling it with a dilute soap solution and sonicating for 10 mm. After sonication, rinse the cuvette ten times with deionized water to remove residual soap. The cuvette should be stored with deionized water in it.

A transmission spectrum of the sample properly diluted relative to the path length used sample is taken (block 102)

with the spectrophotometer, and the data collected are sent to a processor (block 103), wherein standard data from normal controls are resident and may be accessed (block 104). The test and standard data are then normalized (block 105) so that they may be more easily compared. In some cases normalization may not a necessity. The differences are significant enough without normalization.

If the characteristic being examined for has a sufficiently strong signature within the spectrum (block 106), the spectra may be co-plotted (block 107) and a visual determination made (block 108) for the presence of the characteristic. The disease-specific spectral features arise from changes in the size, shape, and chemical composition of the major blood components (blood cells and plasma) caused by the pathogen.

If the characteristic does not have strong signal, or if particular features are desired to be calculated, such as particle size distribution, size, shape, or chemical composition (block 106), spectral deconvolution is performed (block 109), an analysis of the deconvoluted data performed (block 110), and the characteristic of the particulate(s) determined (block 111). This information is used to define elements of classification for the quantification of chemical species, cell enumeration, and the identification of viruses, bacteria, or protozoa of interest, for example, although these are not intended as limitations.

The deconvolution may be accomplished by, for example, calibration based on correlation or with the use of theoretical models based on theories of absorption and scattering of electromagnetic radiation. References authored by some of the present inventors contain disclosure on the analysis of multiwavelength spectroscopic data, and these references are incorporate herein by reference (Brandolin et al., 1991; Chang et al., 1993; Elicabeetai, 1988, 1990; Garcia-Rubio-etai, 1984, 1985, 1987, 1989, 1992, 1993, 1994, 1999; Marquez et al., 1993; Mattley et at., 2000).

As examples, samples may be analyzed for the concentration of several types of hemoglobin, the level of oxygenation, bilirubin, and total hematocrit. It is also possible to identify and classify blood types using their spectral signature and to detect free hemoglobin and other particles present in blood such as abnormal sickling hemoglobin and *Plasmodium* sp. It will also be possible, it is believed, to detect markers of other diseases such as HIV and HBV.

The uv-vis transmission spectra of a large variety of blood samples of different types have been spectroscopically investigated. These spectra have shown that the uv-vis portion of the spectrum contains sufficient information for the statistical identification and classification of blood types and the subsequent identification of blood diseases and the presence of foreign microorganisms. In addition, the spectra establish the reproducibility of the method, permit identification of spectral features associated with healthy blood, and establish appropriate controls for comparison purposes.

Sample spectra of several blood diseases are shown in FIGS. 2–6, with contrasting spectra for normal controls. FIG. 7 and FIG. 8 display tables, 1 and 2, which provide accompanying diagnosis data provided by the Laboratorio Regional de Apoyo Epidemiologica, Valencia, and Venezuela, where the malaria and dengue fever data were obtained.

Figure 2:
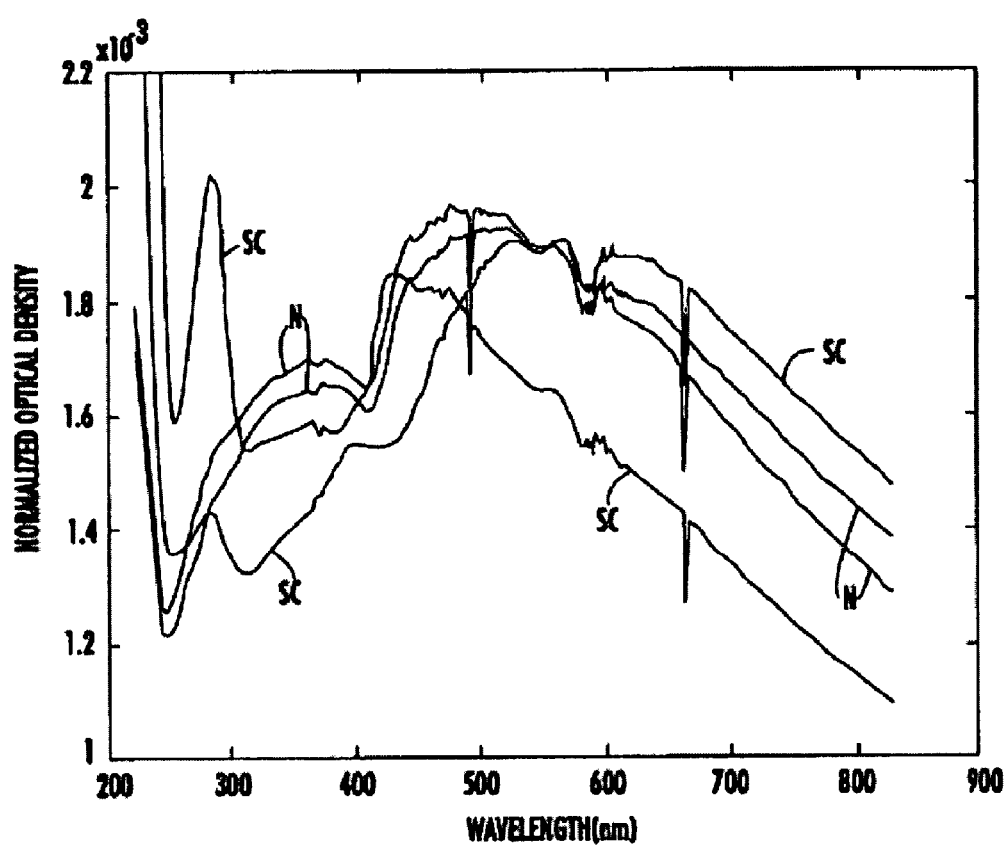
FIG. 2 is an exemplary optical density spectrum for normal and sickle cell red blood cells.

In FIG. 2 are uv-vis spectra of two replicate measurements of normal (N) whole blood together with measurements of whole blood containing sickle cells (SC) from two different patients. Dramatic differences may be noted in the spectral region between 220 and 600 nm, where the main chromophone groups in blood, including nucleic acids, proteins, and liganded metals, are known to absorb. The spectral differences between 600 and 900 nm are also significant in that they reflect changes in the scattering characteristics (size and shape) of the cells. Thus this region of the electromagnetic spectrum is particularly suitable for the detection and identification of particulate(s) with a high degree of specificity.

Figure 3:
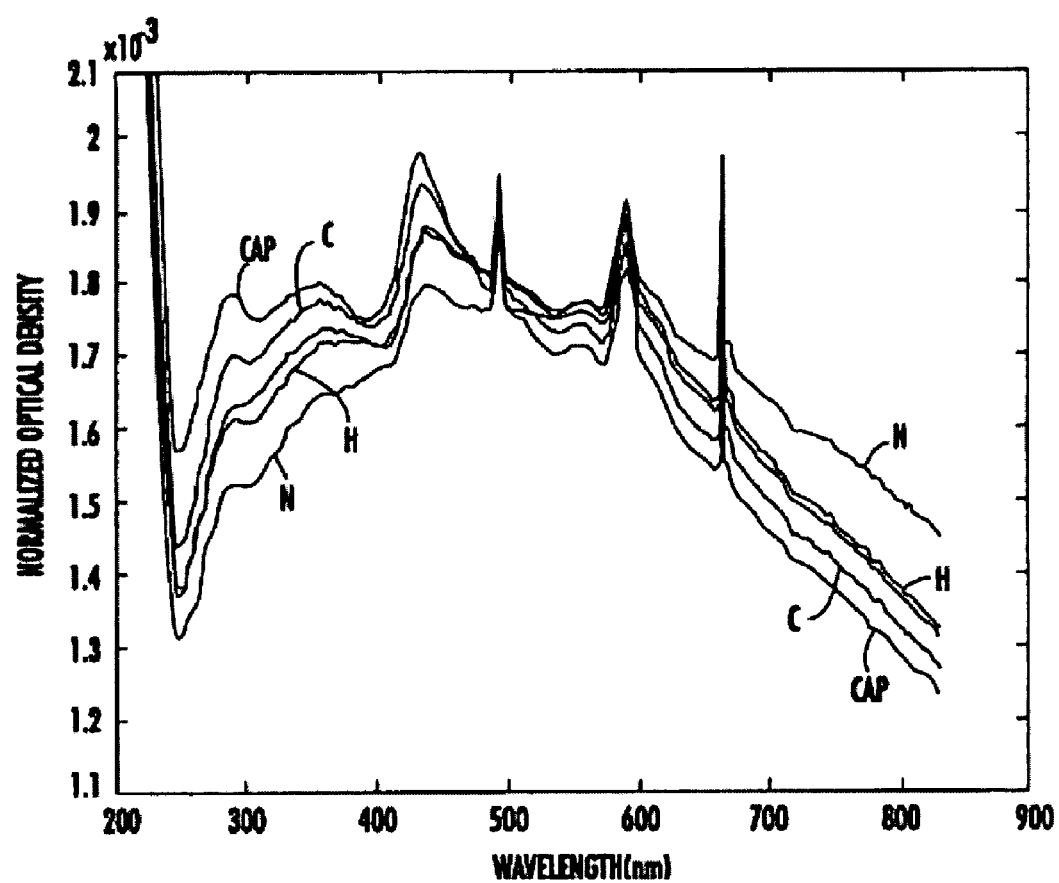
FIG. 3 is an exemplary optical density spectrum for normal and dengue fever patients.

In FIG. 3 spectra of normal (N) whole blood and whole blood from dengue fever patients are shown. The dengue fever patients include hemorrhagic (H), classical acute phase (CAP), and classical (C). Again dramatic differences are shown across the uv-vis spectrum, and there are clear similarities in the absorption and scattering characteristics of the spectra from dengue fever patients' blood. One may also distinguish a patient in the acute phase of the disease.

Figure 4:
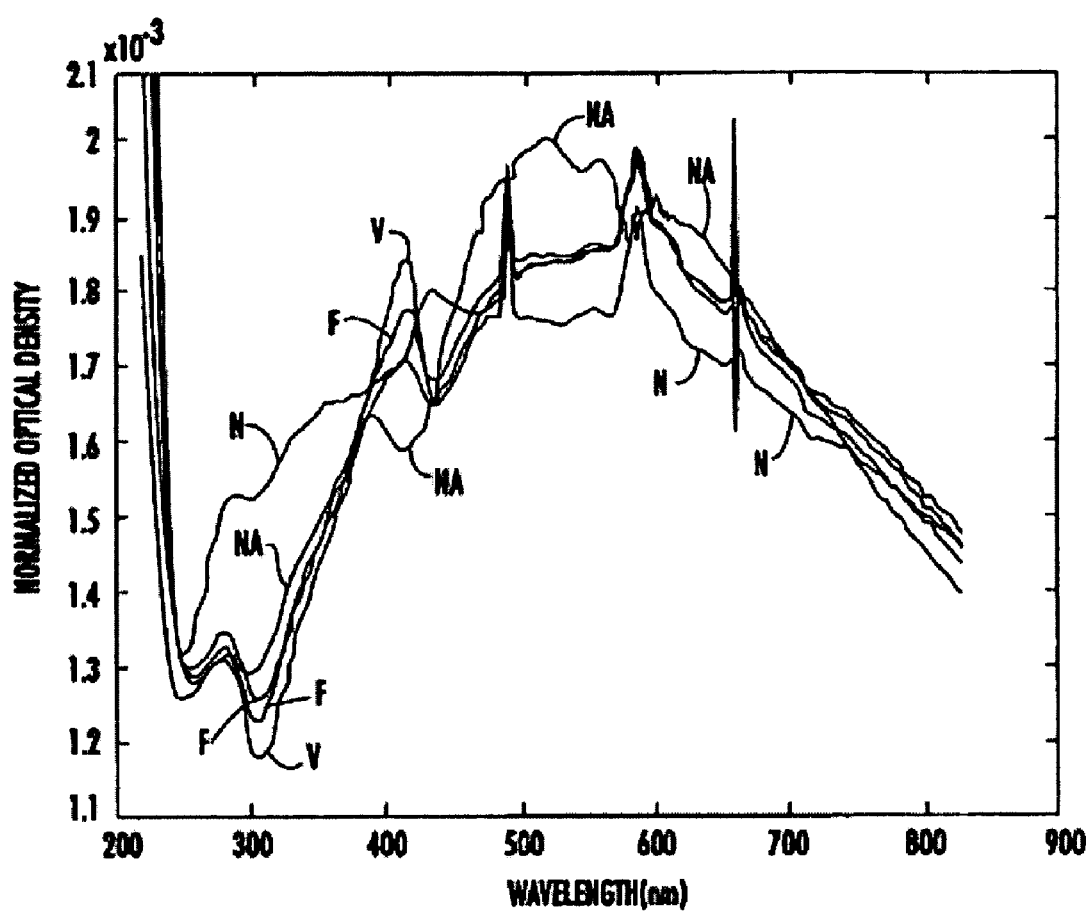
FIG. 4 is an exemplary optical density spectrum for normal and malarial patients.

In FIG. 4 are shown spectra of normal (N) whole blood, aged normal (NA) whole blood, and blood from malarial patients. Dramatic differences in the spectral region between 250 and 600 nm are shown; as above, the changes in the 600–900 nm range are significant in that they reflect changes in the scattering characteristics of the cells. In malarial patients this is to be expected, since it is known that malarial parasites host in red blood cells. There are also clear spectral differences between the two types of malarial parasites, Vivax (V) and Falciparum (F). It is also notable that the age of the blood sample has a clearly discernible effect on the spectra.

From FIGS. 2–4 it may be seen that the system and method of the present invention are capable of identifying and classifying blood-borne diseases. A penetration level, that is, a level of infection, may also be deduced from the magnitude of the signature, which can be seen in FIG. 2, as an example.

Figure 5:
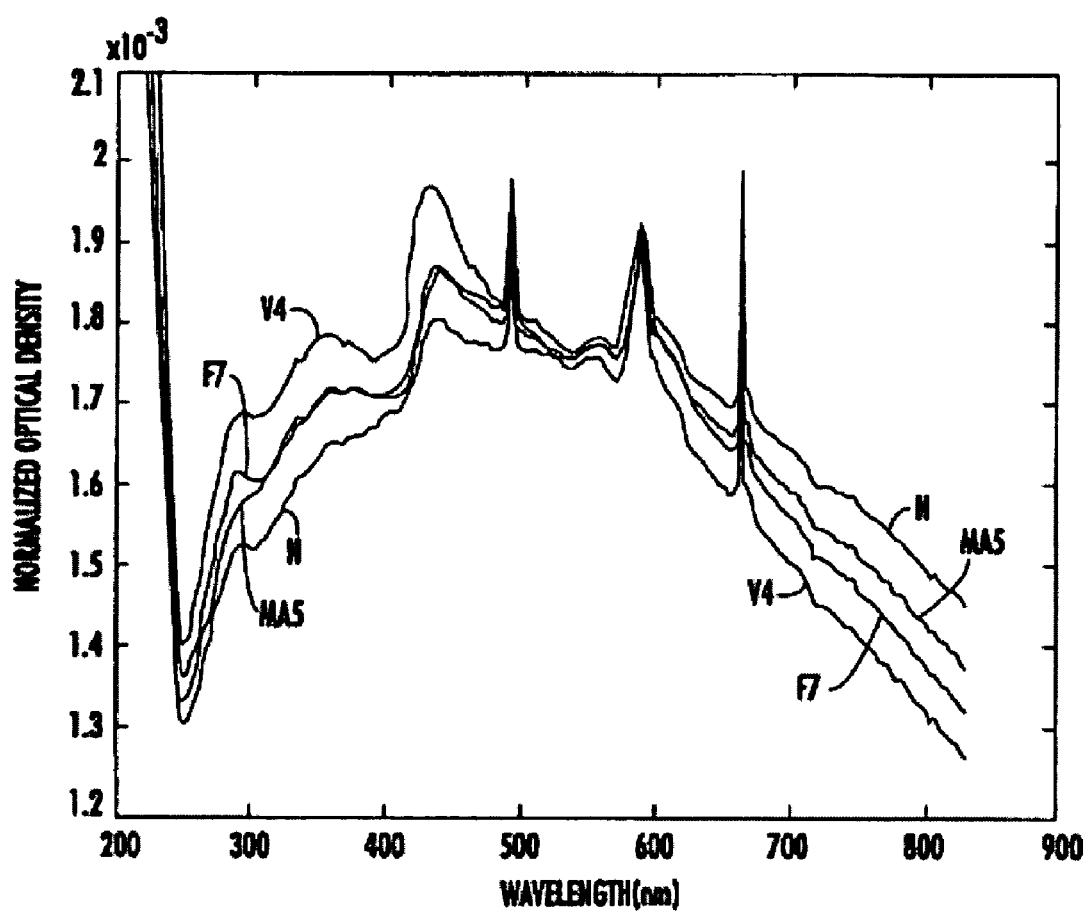
FIG. 5 is an exemplary optical density spectrum for normal and treated malarial patients.

The effect of treatment on the spectrum of whole blood for malarial patients is shown in FIG. 5. The spectra include normal (N), Falciparum treated 7 days (F7), Vivax treated 4 days (V4), suspected malaria and amebiasis treated for 5 days with antibiotics (MA5). Referring back to FIGS. 3 and 4, it may be seen that, as the disease is treated, the spectral characteristics of the blood begin to approach those of normal whole blood.

Thus it may be seen that the present invention can be used to monitor both the extent of the disease and the progress of the treatment.

Figure 6:
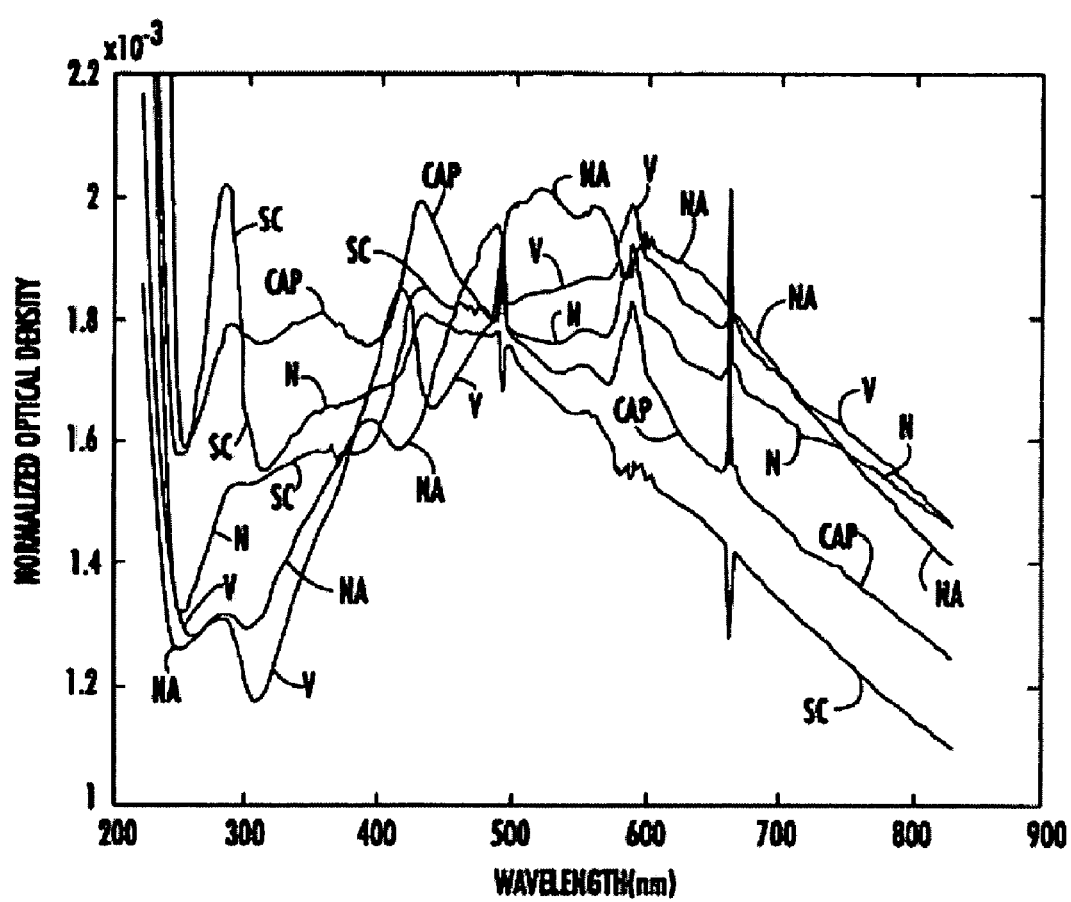
FIG. 6 is an exemplary optical density spectrum for normal, aged, sickle cell, and malarial patients.

Representative samples of fresh healthy whole blood (N), healthy blood aged 6 days (NA), whole blood containing sickle cells (SC), and whole blood from individuals diagnosed with Vivax malaria (V), and dengue fever in the classical acute phase (CAP) are plotted together in FIG. 6 for comparison.

It should be noted that the system and method can also be applied to other bodily fluids or tissues in the diagnosis of syphilis, gonorrhea, HIV, tuberculosis, and onchocerciasis, and for the characterization of micrometer- and submicrometer-sized particles such as may be present in blood and other bodily fluids, such as, but not intended to be limited to, mucus, urine, tear fluid, spinal fluid, menstrual fluid, and amnioticfluid. In spinal fluid, for example, meningitis, both viral and bacterial, would be easily detectable; in urine, microalbuminemia or hyperproteinurea can be detected to suggest a diagnosis of kidney disease.

In a specific embodiment, a method and kit are provided for the detection of albumin and creatinine present in a urine test sample. The main difficulty in the detection of albumin and other proteins arises from small concentrations for which accurate levels of detection are required and the relatively weak absorption coefficients of the protein chromophoric amino acids. The measurement results should be highly specific for albumin and for creatinine, free from interference by other substances in urine, and sensitive and accurate to levels of albumin from 1 microgram albumin/ml urine (0.1 mg/dL, or 1 mg/L) to 4 mg albumin/ml urine (400 mg/dL, or 4 g/L) and for the levels of creatinine from 0.167 mg creatinine/ml urine* (16.7 mg/dL, or 167 mg/L) to 4 mg creatinine/ml urine (400 mg/dL, or 4 g/L). This requires either high concentrations for detection, or the incorporation of stronger chromophores or fluorophores (molecular beacons) to enable spectrophotometric detection. Alternatively the uses of antibodies attached to micro-spheres are also a means of collecting and concentrating the protein and thus enabling detection. Although existing methods have the required sensitivity (reproducible detection down to 10 mg/L) they are expensive and in many instances semi quantitative only. A technique based on protein aggregation followed with multiwavelength spectrophotometric measurements, and/or light scattering photometry, constitutes the basis of this embodiment. The use of specific salts for protein aggregation and precipitation is well established and it is a standard technique for protein fractionation and purification. What has not been used, and constitutes the novelty of this invention is that, when proteins aggregate, there are significant changes in the absorption and scattering properties of the suspension. These changes are quantitative and considerably amplify the spectrophotometric response, thus enabling quantitative detection of down to 10 mg/L. The characterization of the protein aggregates can be accomplished using light scattering and/or multiwavelength spectroscopy.

Figure 9:
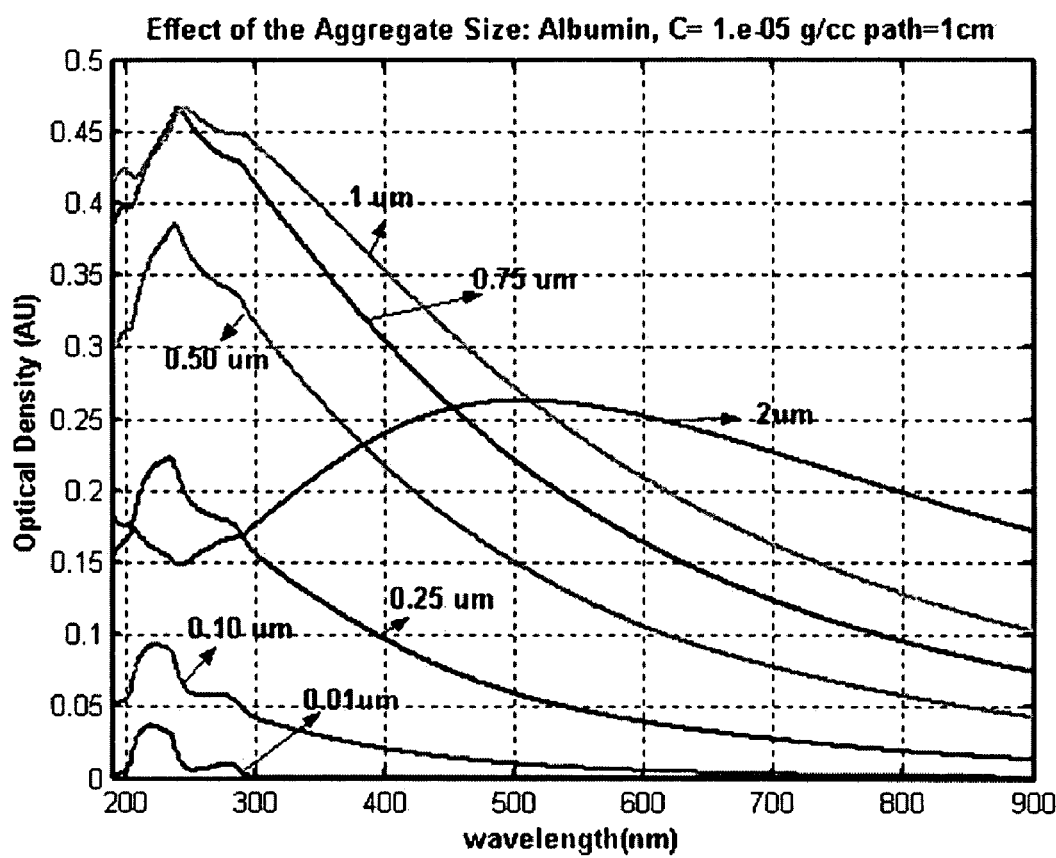
FIG. 9 is an illustration of the theoretically predicted changes in the spectral features of albumin as the protein aggregates from solution and as the size of the aggregates increases.

The potential of the proposed approach for the detection of albumin in urine can be readily appreciated with reference to FIG. 9, where the theoretically calculated transmission spectra of an albumin solution and albumin aggregate suspensions are shown as functions of the aggregate size. The figure represents the expected changes in the spectral features as the protein aggregates from solution and as the size of the aggregates increases. Throughout the process the mass of protein is constant and equal to the protein in solution ($1 \times 10^{-5}$ g/mL). The simulations were conducted using equations 1–5 and a 1 cm pathlength. The aggregate sizes are indicated on the figure. Note that the concentration is in the range of microalbumin, and that, as expected for the protein in solution, the absorption peaks typical of protein amino acids (250 and 280 nm) are rather weak. As the size of the aggregates increases, the strength of the signal also increases to an OD of approximately 0.45 at 250 nm when the protein aggregates are approximately one micron in size. The substantial increase in the signal is due to the considerable increase in the scattering component of the signal as the aggregates grow in size.

The importance of the above results is that by aggregating the proteins their concentration can be readily determined using standard spectrophotometric and/or light scattering instrumentation. Quantitative results can be obtained through a calibration, or through equations 1–5. An additional important feature is that there is adequate signal in the visible portion of the spectrum. This implies considerable simplifications for the instrumentation while leaving the adjustments in pathlength to increase sensitivity or to look at other analytes.

Figure 10:
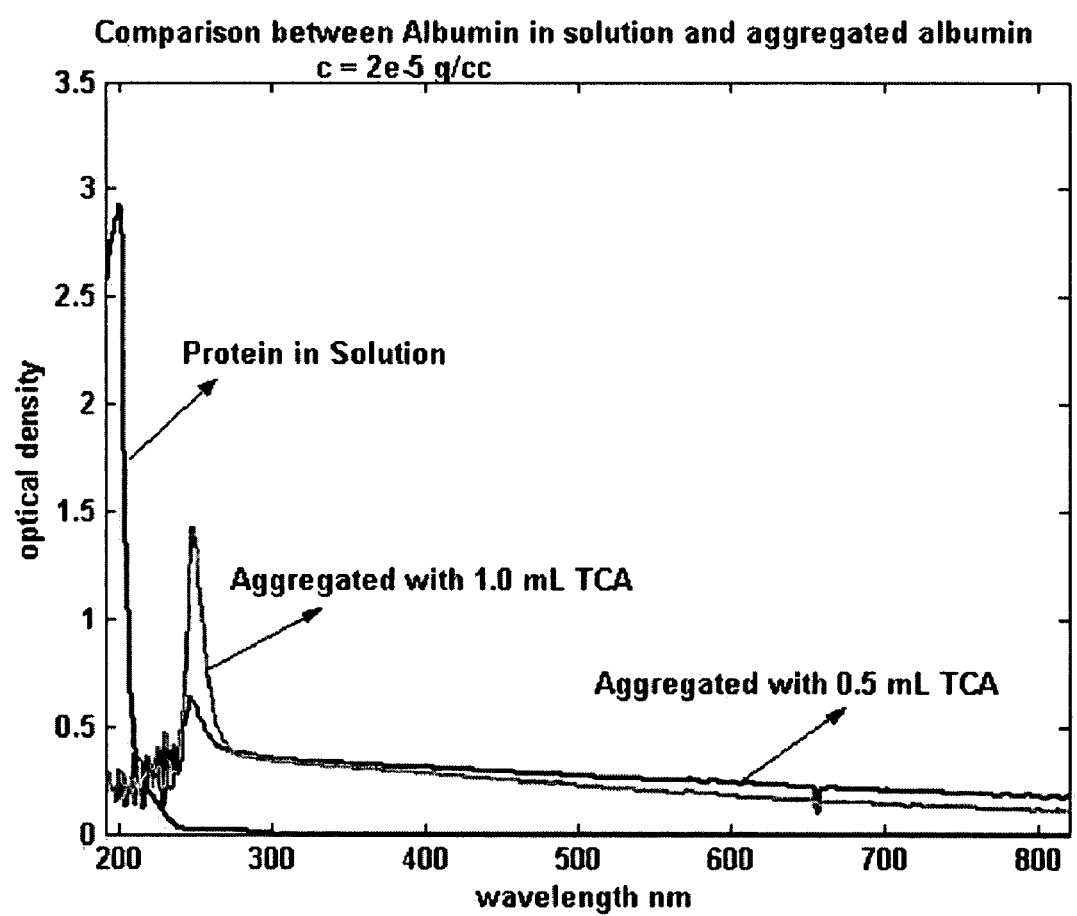
FIG. 10 is a graphical illustration of the experimental demonstration if the signal enhancement due to protein aggregation in accordance with the present invention.
Figure 11:
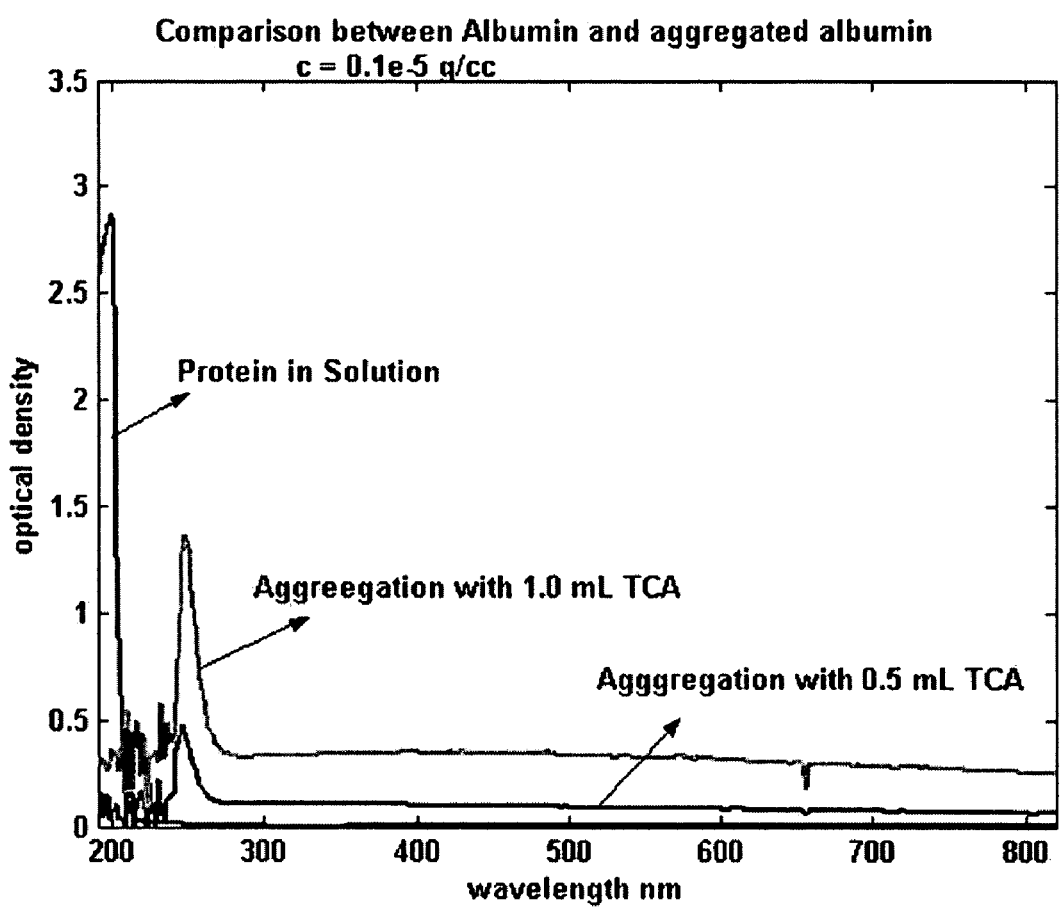
FIG. 11 is a graphical illustration of the signal enhancement due to protein aggregation in accordance with the present invention.

The use of specific salts for protein aggregation and precipitation is well established and it is a standard laboratory technique for protein fractionation and purification. In an exemplary embodiment for the detection of albumin in urine, solutions with known concentrations of bovine albumin were aggregated using trichloroacetic acid (TCA) and the standard procedure used for protein precipitation. The results are shown in FIGS. 10 and 11 for two concentration levels of TCA. Notice that considerable enhancement of the signal is obtained even for albumin concentration levels of the order of $0.1 \times 10^{-5}$ g/mL. Thus enabling the detection and measurement of microabluminuria using spectrophotometric methods. As such, the present invention provides a method comprising the use of induced aggregation of proteins followed by spectrophotometric and/or light scattering measurements for the quantification of proteins in general, and albumin in particular.

In an additional embodiment, the method of the present invention is effective in the identification of spectral differences between contaminated and non-contaminated platelets. In accordance with this embodiment of the invention, platelets were transported at room temperature from Florida Blood Services to the University of South Florida in St. Petersburg. The platelets are maintained at room temperature on an elliptical platelet rotator (Fenwall Laboratories, Deerfield, Ill.). The original sample was divided into two smaller sampling bags (10 ml), a non-spiked and a spiked. The spiked platelet samples are created by adding 2 ml of re-hydrated microorganisms (EZ-cfu, Microbiologics, St. Cloud, Minn.). The bags were sampled hourly to follow the growth of the microorganism and daily for up to seven days post inoculation to follow the aging of platelets. Dilutions were made in saline (30 ul of platelet suspension in 5.47 ml saline) and the dilute suspensions were analyzed on an Hp UV-vis spectrometer (Model 8453). The spectra shown with references to the associated figures were normalized to remove the effects of the number of particles.

Figure 12:
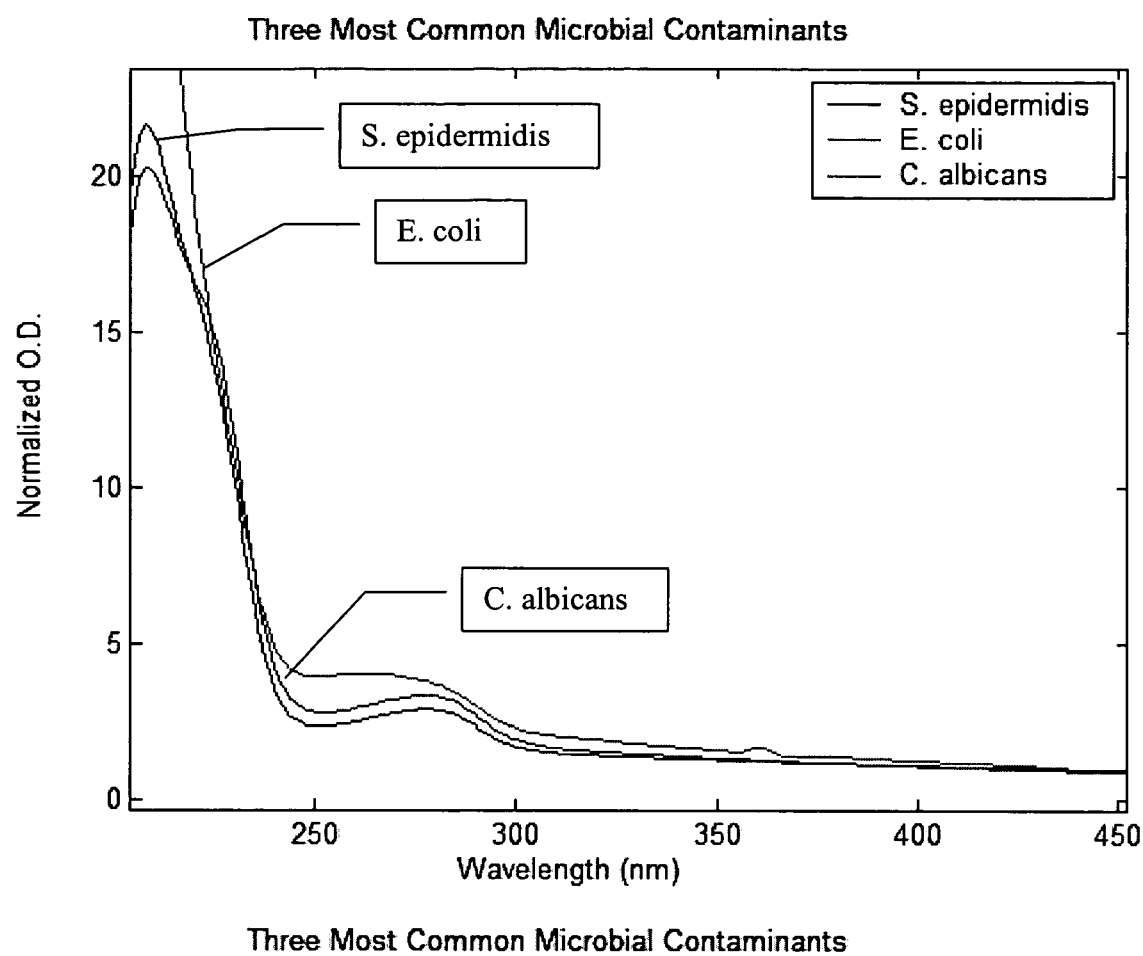
FIG. 12 is a graphical illustration of the normalized optical spectra of the three most common platelet contaminants in accordance with the present invention.
Figure 13:
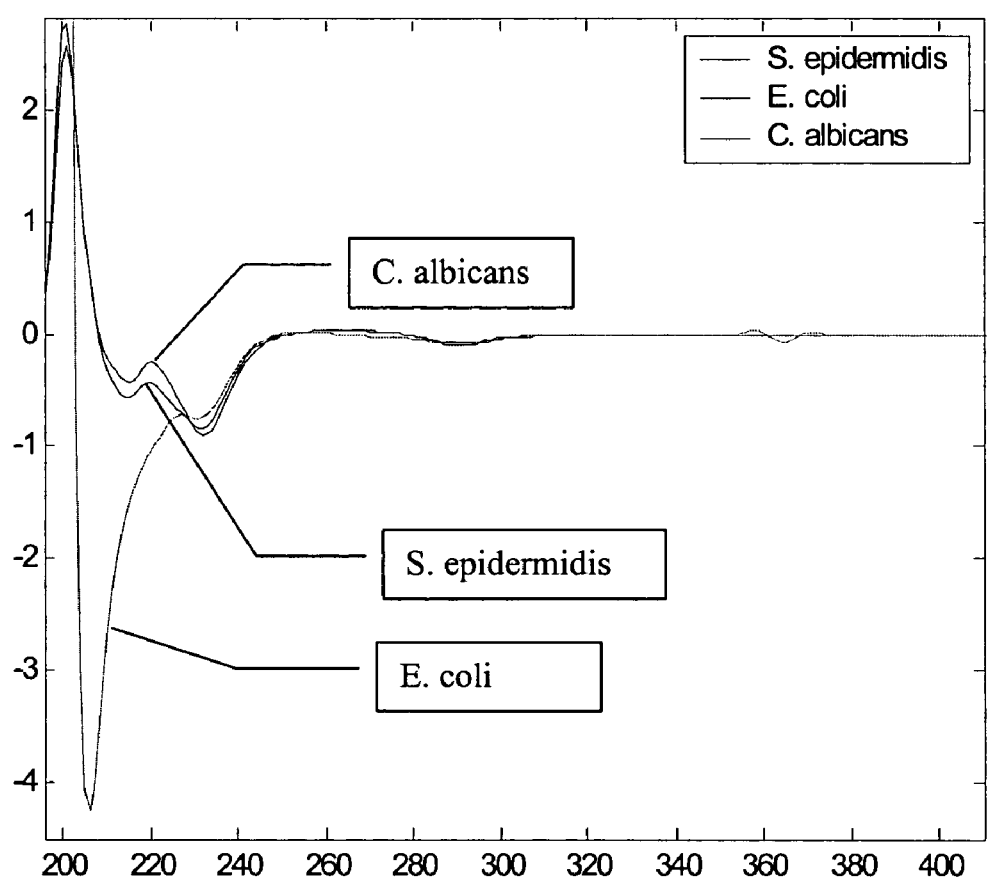
FIG. 13 is a graphical illustration of the first derivative normalized optical density spectra of the three most common platelet contaminants in accordance with the present invention.
Figure 14:
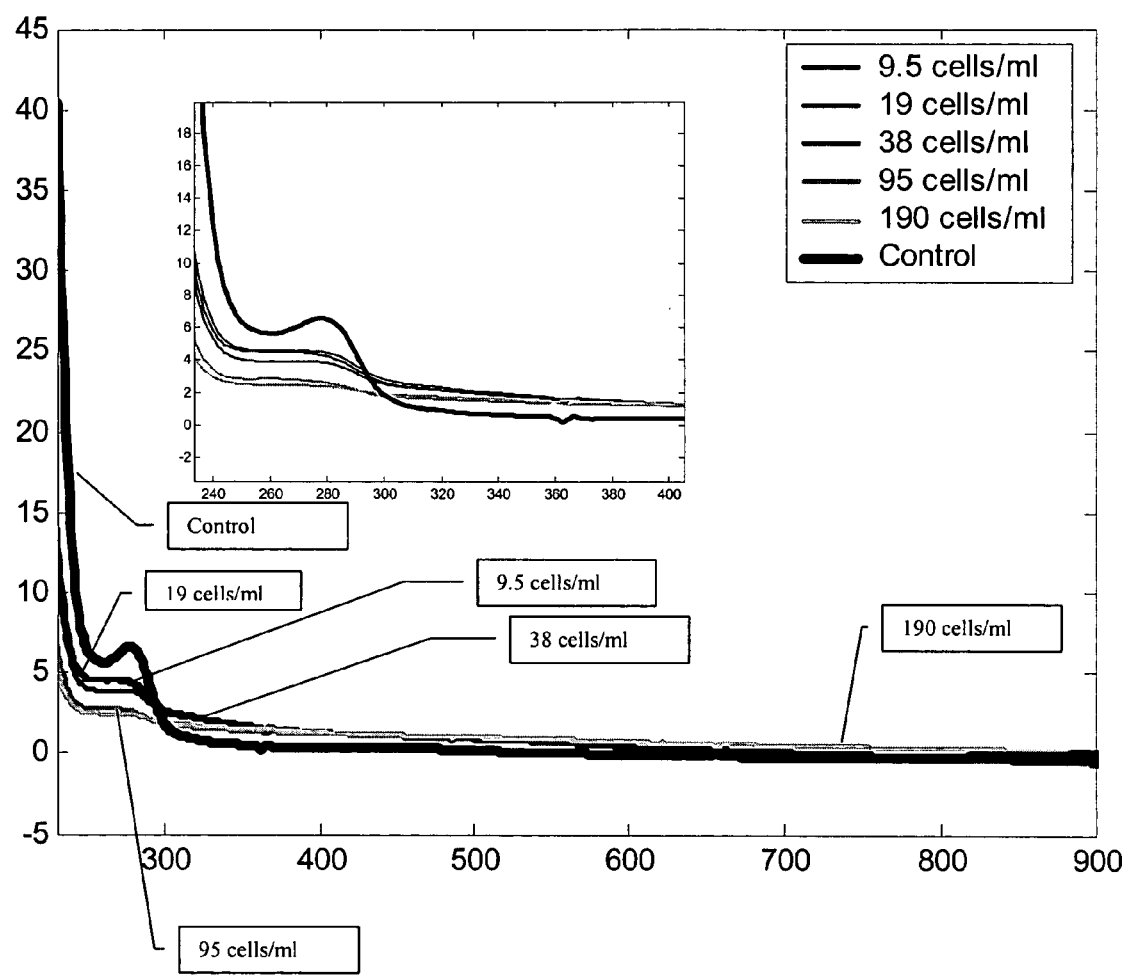
FIG. 14 is a graphical illustration of the comparison of spectra from different concentrations of *E. coli* in accordance with the present invention.
Figure 15:
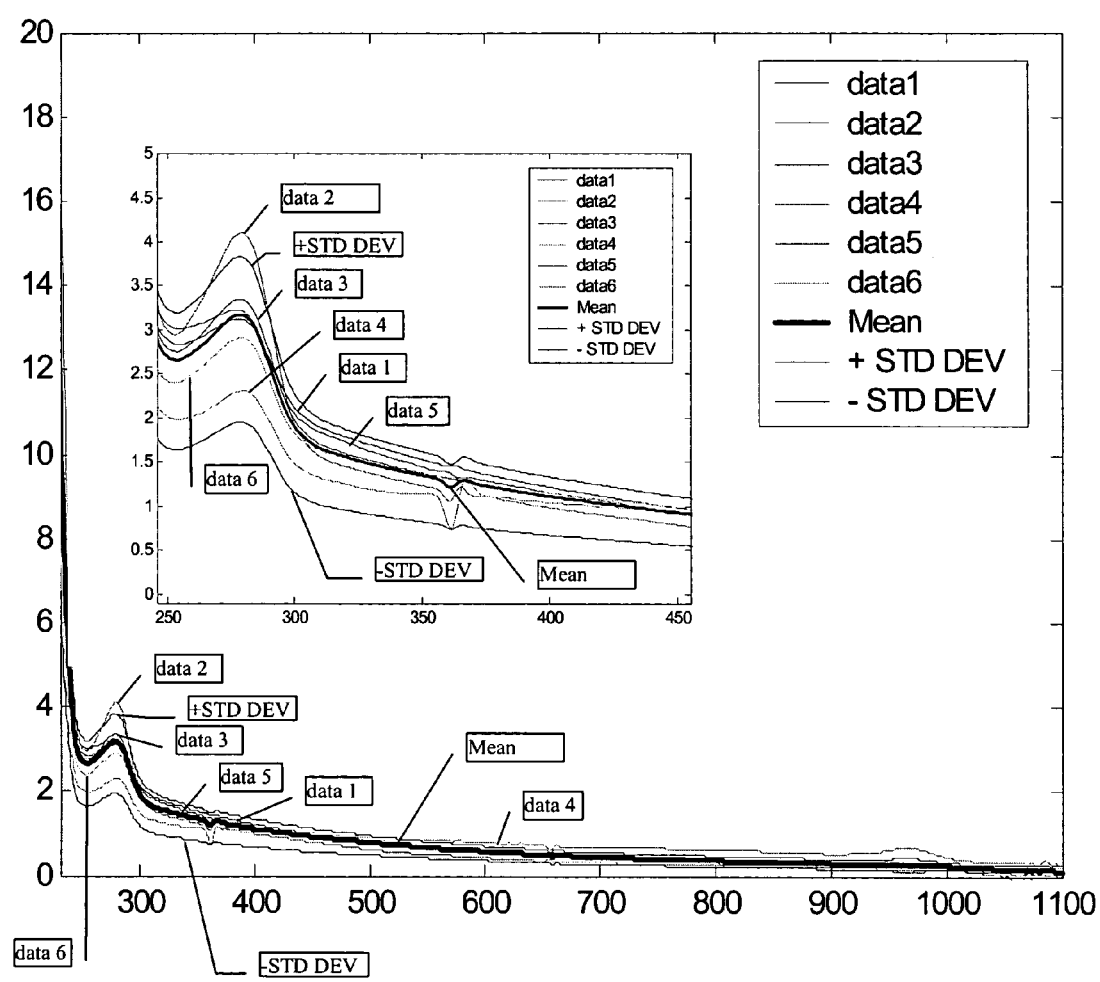
FIG. 15 is a graphical illustration of the spectra from six different platelet suspensions demonstrating the natural variability in uncontaminated platelet samples in accordance with the present invention.

With reference to FIGS. 12–13, the Uv-vis spectra and first derivative spectra of three of the most common platelet microbial contaminants are shown. The first derivative spectra enhance differences in chemical composition and it has been used for microbial identification. FIG. 14 shows a comparison of spectra from samples contaminated with different concentrations of *E. coli* (shown as number of bacterial cells per ml of platelet/plasma suspension). The spectra for theses samples were recorded immediately after being spiked. It is noteworthy that contamination at the level of 95 cells/mL of platelet suspension could be clearly detected. The inset is an enlargement of the 240–400 nm region of the spectra, which further emphasizes the considerable differences present for contaminated and non-contaminated samples. FIG. 15 shows the spectral differences for the samples contaminated at the level 95 cells/mL of platelet suspension.

Figure 16:
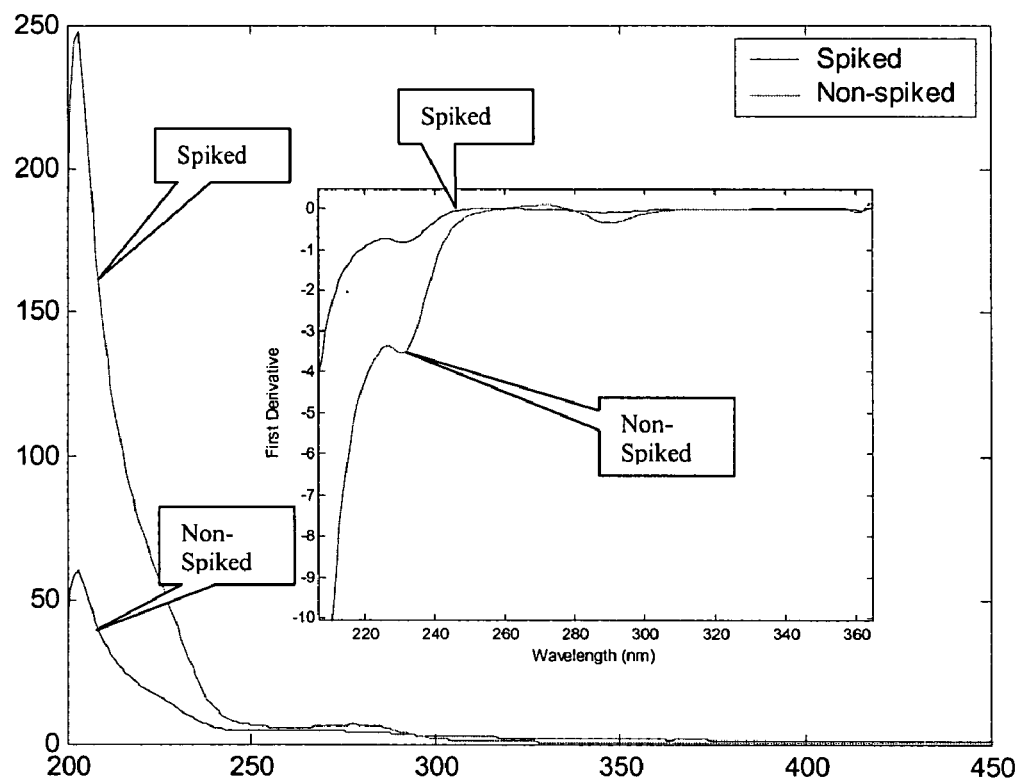
FIG. 16 is a graphical illustration of the comparison of spectra from an uncontaminated platelet sample, and the sample contaminated with a concentration of 95 cells/mL of *E. Coli*. The measurements were take immediately after contamination.
Figure 17:
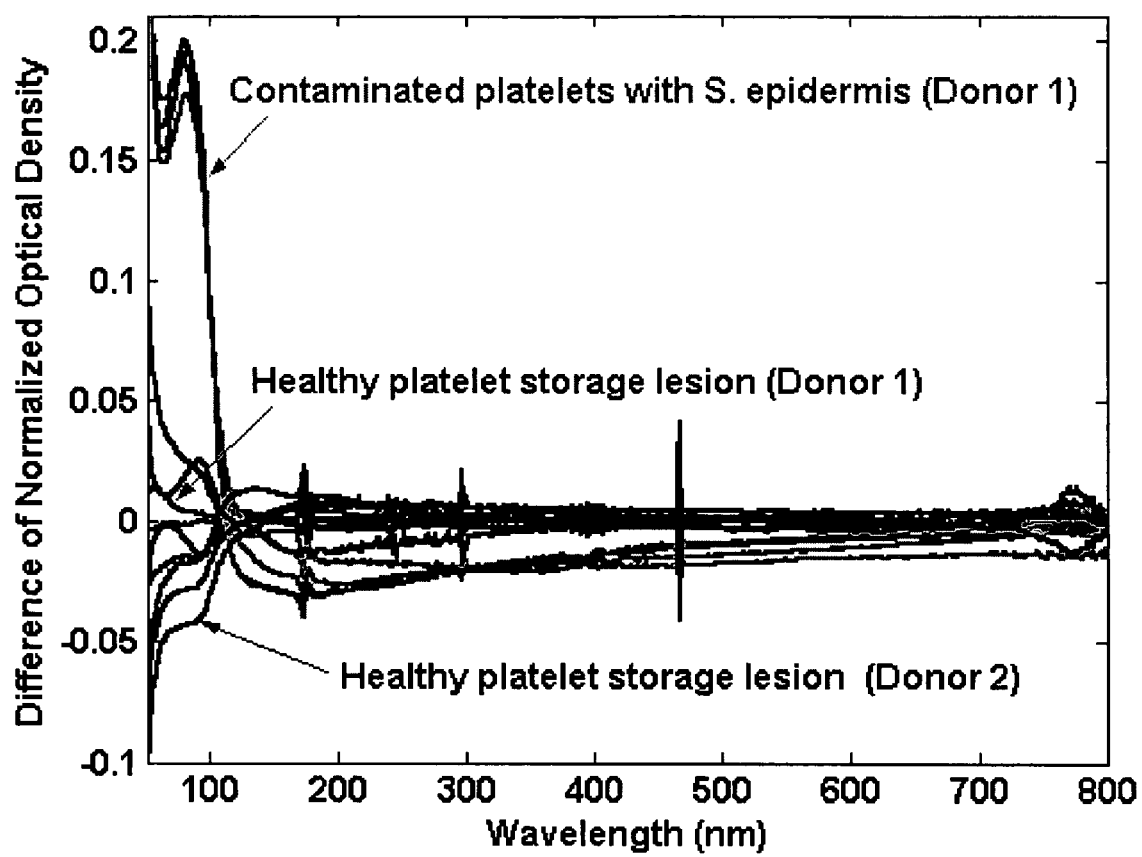
FIG. 17 is a graphical illustration of the data for healthy and contaminated platelets from 2 donors. For this case, the contaminant was *Staphylococus Epidermis*.

FIG. 16 shows the natural variability in the spectra from six different uncontaminated platelet suspensions. The mean is shown in black and +/− one standard deviation is shown in blue. The inset is an enlargement of the 250–450 nm portion of the graph. Notice that even though there is considerable variability there are significant differences in the spectra of contaminated and non-contaminated platelets. The demonstration that these differences are quantitative is reflected in FIG. 17, where the data for healthy and contaminated platelets from 2 donors is presented. The optical difference spectra reported is between the mean normalized optical density of healthy platelets corresponding to each donor and the measured spectra for all the samples. The natural variability of the platelets over time is reflected in the spectral changes observed for each donor and in-between donors. Notice that the signal from the contaminated platelets is clearly discernible. For this case the contaminant was *Staphylococus Epidermis*.

It is believed that the present invention provides a maximum amount of information and also the greatest sensitivity of detection and identification. Samples in a range of 106 particles are being examined simultaneously, and are not merely being counted, as with microscopic methods.

Another advantage of the present invention is speed of analysis. Blood testing by microscopy typically entails a one-week waiting time and requires a trained microscopist to interpret the data. The present invention provides an immediate analysis, which means that treatment can begin immediately, and the patient does not have to make a return trip to the doctor office. Further, the speed of analysis permits on-site use in remote locations and in critical situations such as combat and in an epidemic.

A further advantage of the present invention is the cost. Whereas testing for some disorders or diseases can cost approximately $700, it is believed that the present invention can decrease this amount by two orders of magnitude, owing to lower equipment investment and elimination of the need for highly trained personnel. A laptop computer can accommodate the software required for the system, and a fiber-optic spectrometer is sufficient for data collection. This enables on-site analysis in remote, underdeveloped areas.

In another embodiment of the present invention, the technique of uv-vis spectroscopy is applicable to noninvasive measurements, wherein the absorption, scattering, and polarization properties of the bodily fluid may be studied through the skin.

In yet another embodiment, commercially available metallic beads can be coated with a substance, which will aggregate together if an antibody to the substance exists in the system. Such an aggregation is easily detected with the system and method of the present invention, which can thus be used to test with an immobilized reagent.

In the foregoing description, certain terms have been used for brevity, clarity, and understanding, but no unnecessary limitations are to be implied there from beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for detecting the presence of a protein in a test urine sample, the method comprising the steps of:
   aggregating a test urine sample;
   taking a transmission spectrum of the test urine sample in at least a part of the ultraviolet visible—near-infrared range of the electromagnetic spectrum;
   comparing the transmission spectrum with a theoretically calculated standard urine sample transmission spectrum known to be free from the protein; and
   determining from the comparison whether the urine from the test sample contains the protein.

2. The method recited in claim 1, wherein the protein comprises an agent that alters at least one of a shape, a size, and a chemical composition of a normal urine component.

3. The method recited in claim 1, wherein the comparing step comprises identifying a difference in at least one of a peak height, a peak presence, and a slope between the standard sample and the test sample.

4. The method recited in claim 1, wherein the step of aggregating the test urine sample results in modifications in the absorption and scattering properties of the sample.

5. The method recited in claim 1, wherein the step of aggregating the test urine sample further comprises the addition of a salt to the test urine sample.

6. The method of claim 5, wherein the salt is trichloroacetic acid.

7. The method recited in claim 1, wherein the transmission spectrum has a resolution of at least 2 nm.

8. The method recited in claim 1, wherein the comparing step comprises identifying a feature of the standard spectrum known to change in a presence of the protein and the determining step comprises analyzing the test spectrum for a change in the identified feature.

9. The method recited in claim 1, further comprising the step, prior to the comparing step, of normalizing the standard spectrum and the test spectrum for facilitating the comparing step.

10. The method recited in claim 1, further comprising the step, of adjusting a path length in the spectrum taking step to an optical density range in which the response of the spectrometer is substantially linearly related to the concentration of the sample.

11. The method of claim 1, wherein the protein is albumin.

12. The method of claim 1, wherein the protein is creatinine.

13. A method of quantifying a protein in a test urine sample comprising the steps of:
   aggregating a test urine sample;
   taking a transmission spectrum of the test urine sample in at least a portion of the ultraviolet visible near-infrared range of the electromagnetic spectrum;
   deconvolving the spectrum into absorption and scattering components; and
   determining from the deconvolution a presence and a concentration of a protein in the urine sample.

14. The method recited in claim 13, wherein the protein is albumin.

15. The method recited in claim 13, wherein the protein is creatinine.

16. The method recited in claim 13, wherein the step of aggregating the test urine sample results in modifications in the absorption and scattering properties of the sample.

17. The method recited in claim 13, wherein the step of aggregating the test urine sample further comprises the addition of a salt to the test urine sample.

18. The method of claim 17, wherein the salt is trichloroacetic acid.

19. The method recited in claim 13, wherein the spectrum taking step comprises taking a spectrum in a range of approximately 220–900 nm.

20. The method recited in claim 13, wherein the deconvolving step comprises utilizing a calibration approach based on correlation.

21. The method recited in claim 13, wherein the deconvolving step comprises utilizing absorption and scattering theories.

22. A urine test kit for detecting the presence of a protein, the test kit comprising:
   aggregating reagents;
   a spectrophotometer for taking a transmission spectrum of a test urine sample in at least a portion of the ultraviolet visible near-infrared range of the electromagnetic spectrum;

an analyzer for accessing a standard spectrum from a urine sample known to be free from the protein for comparing the test urine sample transmission spectrum with the standard urin sample spectrum to determine whether the urine from the test sample contains the protein.

23. The urine test kit recited in claim 22, wherein the analyzer comprises a processor and a storage medium in electronic communication with the processor, the storage medium having stored thereon a database of standard spectra.

24. The urine test kit recited in claim 22, wherein the analyzer further comprises a software package resident on the processor having a routine for performing spectral deconvolution of the standard spectrum and the test spectrum, for identifying features of the test spectrum associated with the protein.

25. The urine test kit recited in claim 22, wherein the analyzer further comprises an output device in electronic communication with the processor for providing the standard spectrum and the test spectrum in visible form.

26. The urine test kit recited in claim 22, wherein the aggregating reagent is a salt.

27. The urine test kit recited in claim 22, wherein the aggregating reagent is trichloroacetc acid.

28. The urine test kit recited in claim 22, wherein the protein is albumin.

29. The urine test kit recited in claim 22, wherein the protein is creatinine.

30. A method for detecting the presence of a particle in a plasma test sample, the method comprising the steps of:
taking a transmission spectrum of the test plasma sample in at least a part of the ultraviolet visible—near-infrared range of the electromagnetic spectrum;
comparing the transmission spectrum of the test plasma sample with a theoretically calculated standard plasma sample transmission spectrum known to be free from the particle of interest; and
determining from the comparison whether the plasma from the test sample contains the particle of interest.

31. The method recited in claim 30, wherein the particle comprises an agent that alters at least one of a shape, a size, and a chemical composition of a normal plasma component.

32. The method recited in claim 30, wherein the comparing step comprises identifying a difference in at least one of a peak height, a peak presence, and a slope between the standard sample and the test sample.

33. The method recited in claim 30, wherein the particle is a platelet.

34. The method recited in claim 30, wherein the particle is a microorganism.

35. The method recited in claim 30, wherein the transmission spectrum has a resolution of at least 2 nm.

36. The method recited in claim 30, wherein the comparing step comprises identifying a feature of the standard spectrum known to change in a presence of the particle and the determining step comprises analyzing the test spectrum for a change in the identified feature.

37. The method recited in claim 30, further comprising the step, prior to the comparing step, of normalizing the standard spectrum and the test spectrum for facilitating the comparing step.

38. The method recited in claim 30, further comprising the step, of adjusting a path length in the spectrum taking step to an optical density range in which the response of the spectrometer is substantially linearly related to the concentration of the sample.

39. A method of quantifying a particle in a test plasma sample comprising the steps of:
taking a transmission spectrum of the test plasma sample in at least a portion of the ultraviolet visible near-infrared range of the electromagnetic spectrum;
deconvolving the spectrum into absorption and scattering components; and
determining from the deconvolution a presence and a concentration of a particle in the plasma sample.

40. The method recited in claim 39, wherein the particle is a platelet.

41. The method recited in claim 39, wherein the particle is a microorganism.

42. The method recited in claim 39, wherein the spectrum taking step comprises taking a spectrum in a range of approximately 220–900 nm.

43. The method recited in claim 39, wherein the deconvolving step comprises utilizing a calibration approach based on correlation.

44. The method recited in claim 39, wherein the deconvolving step comprises utilizing absorption and scattering theories.

45. A plasma test kit for detecting the presence of a particle, the test kit comprising:
a spectrophotometer for taking a transmission spectrum of a test plasma sample in at least a portion of the ultraviolet visible near-infrared range of the electromagnetic spectrum;
an analyzer for accessing a standard spectrum from a plasma sample known to be free from the particle for comparing the test plasma sample transmission spectrum with the standard plasma sample spectrum to determine whether the plasma from the test sample contains the particle of interest.

46. The plasma test kit recited in claim 45, wherein the analyzer comprises a processor and a storage medium in electronic communication with the processor, the storage medium having stored thereon a database of standard spectra.

47. The plasma test kit recited in claim 45, wherein the analyzer further comprises a software package resident on the processor having a routine for performing spectral deconvolution of the standard spectrum and the test spectrum, for identifying features of the test spectrum associated with the particle.

48. The plasma test kit recited in claim 45, wherein the analyzer further comprises an output device in electronic communication with the processor for providing the standard spectrum and the test spectrum in visible form.

49. The plasma test kit recited in claim 45, wherein the particle of interest is a platelet.

50. The urine test kit recited in claim 45, wherein the particle of interest is a microorganism.

* * * * *